United States Patent [19]

Doumenis

[11] Patent Number: 4,729,762
[45] Date of Patent: Mar. 8, 1988

[54] THREE STAGE IMPLANTABLE PRESSURE RELIEF VALVE WITH ADJUSTABLE VALVE STEM MEMBERS
[75] Inventor: Demetrios Doumenis, Miami, Fla.
[73] Assignee: Cordis Corporation, Miami, Fla.
[21] Appl. No.: 812,780
[22] Filed: Dec. 23, 1985
[51] Int. Cl.⁴ .......................................... A61M 27/00
[52] U.S. Cl. ...................................... 604/10; 137/504; 137/508
[58] Field of Search ............... 137/504, 859, 508; 604/6-8, 247

[56] References Cited

U.S. PATENT DOCUMENTS

| | | | |
|---|---|---|---|
| 28,722 | 6/1860 | Whitacker | 137/508 |
| 79,436 | 6/1868 | Bechtel | 137/508 |
| 1,139,455 | 5/1915 | Gase | 137/508 |
| 1,159,214 | 11/1915 | Gueux | 137/508 |
| 1,199,152 | 9/1916 | Bruce | 137/508 |
| 1,468,434 | 9/1923 | Zander | . |
| 2,207,382 | 7/1940 | McNamara | 277/21 |
| 2,290,151 | 7/1942 | McCollum | 237/12.3 |
| 2,684,081 | 7/1954 | Chace | 137/859 X |
| 2,960,109 | 11/1960 | Wilson | 137/517 |
| 2,969,066 | 1/1961 | Holter et al. | 128/350 |
| 3,109,429 | 11/1963 | Schwartz | 128/350 |
| 3,233,610 | 2/1966 | Wade | 128/350 |
| 3,270,771 | 9/1966 | Morgan | 137/525.3 |
| 3,288,142 | 11/1966 | Hakim | 128/350 |
| 3,308,798 | 3/1967 | Snider | 123/119 |
| 3,492,996 | 2/1970 | Fountain | 128/350 |
| 3,566,875 | 3/1971 | Stoehr | 128/350 |
| 3,601,128 | 8/1971 | Hakim | 128/350 |
| 3,654,932 | 4/1972 | Newkirk et al. | 128/350 V |
| 3,674,050 | 7/1972 | Kuffer et al. | 137/536 |
| 3,683,929 | 8/1972 | Holter | 128/350 V |
| 3,756,243 | 9/1973 | Schulte | 128/350 V |
| 3,768,508 | 10/1973 | Schulte | 137/522 |
| 3,769,982 | 11/1973 | Schulte | 128/350 |
| 3,782,410 | 1/1974 | Steuby | 137/496 |
| 3,804,113 | 4/1974 | Garcea | 137/496 |
| 3,827,439 | 8/1974 | Schulte et al. | 128/350 |
| 3,886,948 | 6/1975 | Hakim et al. | 128/350 V |
| 3,889,687 | 6/1975 | Harris | 128/350 V |
| 3,901,245 | 8/1975 | Spitz et al. | 128/350 V |
| 3,924,635 | 12/1975 | Hakim | 128/350 V |
| 3,970,105 | 7/1976 | Pelton et al. | 137/498 |
| 3,985,140 | 10/1976 | Harris | 128/350 V |
| 3,991,768 | 11/1976 | Portnoy | 128/350 |
| 3,999,553 | 12/1976 | Spitz | 128/350 |
| 4,103,689 | 8/1978 | Leighton | 128/350 V |
| 4,106,510 | 8/1978 | Hakim et al. | 128/350 V |
| 4,156,422 | 5/1979 | Hildebrandt et al. | 128/748 |
| 4,167,952 | 9/1979 | Reiniecke | 137/493 |
| 4,215,695 | 8/1980 | Spitz et al. | 128/350 |
| 4,246,930 | 1/1981 | Bishop | 137/493.9 |
| 4,332,255 | 6/1982 | Hakim et al. | 128/350 |
| 4,340,038 | 7/1982 | McKean | 128/1.3 |
| 4,437,493 | 3/1984 | Okuda et al. | 138/45 |
| 4,443,214 | 4/1984 | Marion | 604/9 |
| 4,452,423 | 6/1984 | Bevlavi | 251/65 |
| 4,551,128 | 11/1985 | Hakim et al. | 137/508 X |
| 4,627,832 | 12/1986 | Hooven et al. | 137/508 X |

FOREIGN PATENT DOCUMENTS 68509 8/1951 Netherlands .

Primary Examiner—Dalton L. Truluck
Attorney, Agent, or Firm—Lockwood, Alex, FitzGibbon & Cummings

[57] ABSTRACT

An implantable valve for controlling the passage of cerebrospinal fluid (CSF) from a ventricle of the brain to a suitable drainage location in the body includes a movable diaphragm, one side of which is in the pressure communication with the drainage location of the body, and the other side of which is in pressure communication with the ventricular spaces of the brain. A valve assembly, actuable by displacement of the diaphragm in response to applied pressure differentials, regulates passage of CSF from the ventricular spaces to the drainage location. When the pressure differential falls below a minimum threshold level, the valve is closed to prevent fluid flow. When the pressure differential increases beyond the threshold, the valve operates in a constant pressure mode to maintain a first predetermined pressure differential across the valve. In response to an increase in differential pressure beyond an intermediate threshold level, the valve mechanism operates in a constant flow mode to maintain a desired relatively constant CSF flow rate through the valve. Above a predetermined maximum pressure differential, the valve operates in a constant pressure mode to maintain a second predetermined maximum pressure differential across the valve. To provide for adjustment of the flow characteristics of the valve in the various modes, the valve stem is provided with multiple adjustment means.

4 Claims, 10 Drawing Figures

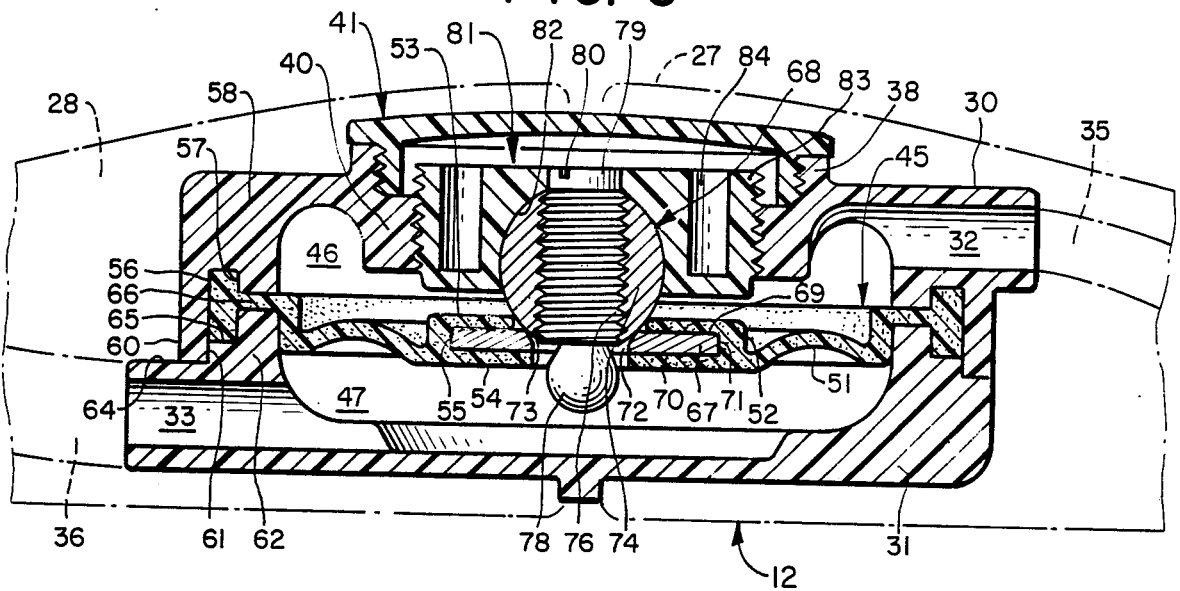
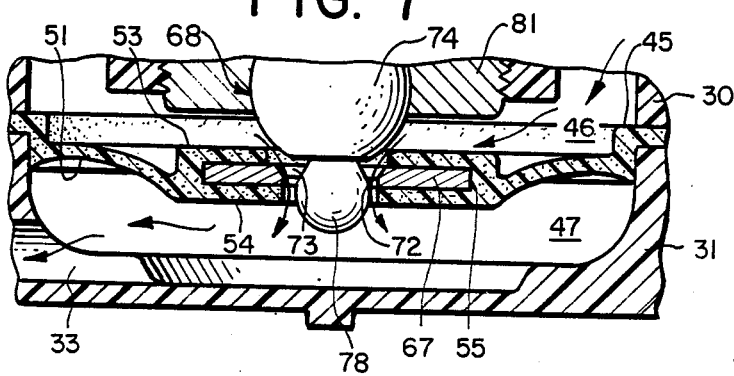
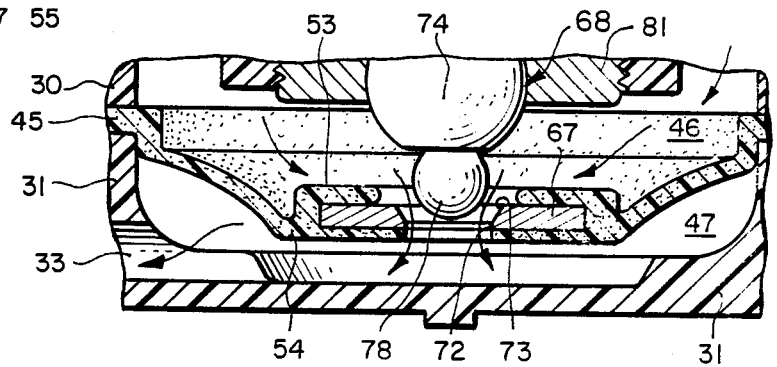
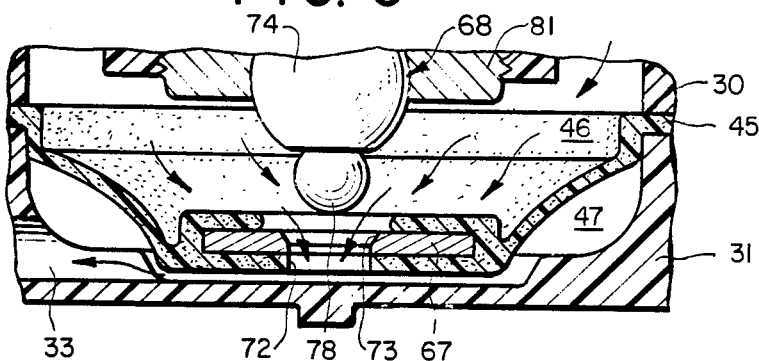

THREE STAGE IMPLANTABLE PRESSURE RELIEF VALVE WITH ADJUSTABLE VALVE STEM MEMBERS

BACKGROUND OF THE INVENTION

The present invention relates to an intracranial pressure relief valve and, more particularly, to a three stage valve having adjustable valve stem members which not only adjust closing pressure but also regulate fluid flow during three stage operation of the valve.

Hydrocephalus is a condition in which the body, for any one of a variety of reasons, is unable to relieve itself of excess cerebrospinal fluid (CSF) collected in the ventricles of the brain. The excessive collection of CSF in the ventricles results in an abnormal increase in both epidural and intradural pressures. This may in turn cause a number of adverse physiological effects including compression of the brain tissue, impairment of blood flow in the brain tissue, and impairment of the brain's normal metabolism.

Treatment of a hydrocephalic condition frequently involved relieving the abnormally high intracranial pressure. To this end, a variety of CSF pressure regulator valves and methods of controlling CSF pressure have been developed which include various check valves, servo valves or combinations thereof. Generally, such valves serve to divert CSF from the ventricles of the brain through a discharge line to some suitable drainage location in the body, such as the venous system or the peritoneal cavity. The check valves operate by opening when the difference between CSF pressure and pressure in the discharge line exceeds a predetermined level.

The use of a simple check valve in the treatment of hydrocephalus is potentially disadvantageous since it is possible for such a valve to open in response to a sudden, but nevertheless perfectly normal, increase in differential pressure between CSF in the ventricular spaces and fluid at the selected discharge location of the body, resulting in abnormal and potentially dangerous hyperdrainage of the ventricular spaces. For example, when a patient stands after lying in a recumbent position, the resulting increased vertical height of the fluid column existing between the head and the selected drainage location may result in such an increase in differential pressure. Accordingly, valves, such as that described in the copending application of the present inventor, Ser. No. 672,868, filed Nov. 19, 1984, have been developed which serve to prevent undesired hyperdrainage by limiting the flow rate of fluid through the valve when a sudden increase in differential pressure occurs.

In this valve, a diaphragm is movable in response to the pressure differential between ventricular CSF pressure in an outlet chamber on one side of the diaphragm, and the pressure of fluid at the drainage location of the body in an outlet chamber on the other side of the diaphragm. The diaphragm has a valve seat which forms a fluid metering orifice. The valve stem extends through the orifice to provide fluid metering between the two chambers. The motion of the diaphragm in response to changes in differential pressure in the valve chambers cause the valve seat to move from a first position, in which the valve seat engages a section of the valve stem to provide a first valve condition in which the orifice is blocked and fluid flow is prevented within the diaphragm moves the valve seat to a second position, in response to an increased pressure differential between the two chambers a second valve condition is provided in which fluid flow between the chambers is sufficient to maintain a first substantially constant predetermined pressure in the first chamber. In response to a sudden increase in differential pressure, such as might be caused by a drastic change in the position of the patient, such as movement from a recumbent position to a vertical position, the diaphragm and valve seal move relative to the valve stem assembly to establish a third valve condition wherein flow between the chambers is controlled at a substantially constant flow rate. In order to prevent hyperdrainage, any further movement of the diaphragm and valve seat relative to the valve stem creates a fourth valve condition wherein a second substantially constant predetermined pressure in the first chamber is maintained.

A CSF pressure relief valve is typically miniaturized for implantation and is required to perform with a high degree of precision under highly demanding conditions throughout a rather extensive, ever-changing mode of operation. Consequently, it has been necessary to carefully control the dimensions of the various parts of the valve, particularly the valve seat, the valve stem assembly and the orifice defined by the valve seat. The parts involved are quite small, and working tolerances on the order of 0.0001 of an inch must be met. Considerable manufacturing costs may be incurred in constructing such a valve.

A CSF pressure relief valve incorporating a one piece valve stem is described in the copending application of the present inventor, Ser. No. 609,137, filed May 8, 1984. An alternative construction for the valve members is described in the copending application of the present inventor entitled Three Stage Intracranial Pressure Control Valve filed concurrently herewith. The present invention is directed to an improvement in the valving mechanism, particularly the valve stem assembly, and, in conjunction therewith, the valve seat and the orifice defined thereby. Basically, this improvement utilizes one or more adjustment means operative with respect to the valve stem assembly so as to permit external adjustment of certain parts thereof to not only adjust the closing pressure of the valve, but also to adjust the fluid flow response of the valve in carrying out the multiple conditions of fluid flow operation. For example, by utilization of the adjustment features of the valve of the present invention, certain tolerances can be eliminated or made less critical and, as a result, the cost of the valve can be reduced. Other advantages will become apparent from the following detail description.

In view of the foregoing, it is a general object of the present invention to provide a new and improved pressure regulator valve for relieving intracranial pressure caused by the presence of excess CSF in the ventricles of the brain.

It is a more specific object of the present invention to provide a pressure regulator valve which includes components which may be more easily and economically manufactured.

It is a still more specific object of the present invention to provide a pressure regulator valve in which there is an improved mechanically adjustable relationship between the valve stem assembly or certain parts thereof and the valve seat carried on the diaphragm and defining the fluid flow orifice.

SUMMARY OF THE INVENTION

The invention is directed to a valve for controlling the passage of body fluids from one location in the body to another location. The valve includes a housing having first and second interior chambers. An inlet port establishes fluid communication between the first chamber and the one location, while an output port establishes fluid communication between the second chamber and the other location. A valve mechanism, including a functionally single-piece valve stem having a valve closure surface and a fluid flow control and restrictor portion formed thereon, located between the first chamber and second chamber, is functional relative to a movable valve seat to establish a first condition in which fluid communication between the first and second chambers is prevented. This first condition is brought about by engagement of a portion of the valve mechanism with the valve seat which is carried on a movable diaphragm within the housing, the diaphragm dividing the housing into the first and second chambers. The valve seat is configured to not only cooperate with the valve mechanism to establish the first condition described but also to cooperate with the valve mechanism throughout the operation of the valve in defining fluid flow. In this environment, the valving arrangement is also actuable to a second condition in which fluid communication is provided between the first and second chambers at a flow rate sufficient to maintain a substantially constant desired first pressure in the first chamber, and to a third condition in which fluid communication is provided between the first and second chambers sufficient to maintain a desired substantially constant fluid flow rate. Finally, the valving arrangement is actuable to a fourth condition in which fluid communication is provided between the first and second chambers sufficient to maintain a substantially constant desired second pressure in the first chamber. The valve mechanism of the arrangement includes one or more adjustment means to permit variation of the sequentially conditioning of the flow of fluid in the second through fourth conditions of fluid flow independently of the first condition of fluid flow. In the preferred form of the valve mechanism, there are two independently adjustable parts, the first part being in the form of a valve closure means functioning to establish the first condition of fluid flow, and the second apart being in the form of a valve pin means which is primarily responsible for the second through four conditions of fluid flow.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 6 is an enlarged cross-sectional view of the pressure regulator valve taken along lines 6—6 of FIG. 5.

FIG. 7 is a cross-sectional view, similar to FIG. 6, showing the pressure regulator valve in a first constant pressure mode.

FIG. 8 is a cross-sectional view, similar to FIG. 6, showing the pressure regulator valve in a constant flow rate mode.

FIG. 9 is a cross-sectional view, similar to FIG. 6, showing the pressure regulator valve in a second constant pressure mode.

DESCRIPTION OF THE PREFERRED EMBODIMENT

Figure 1:
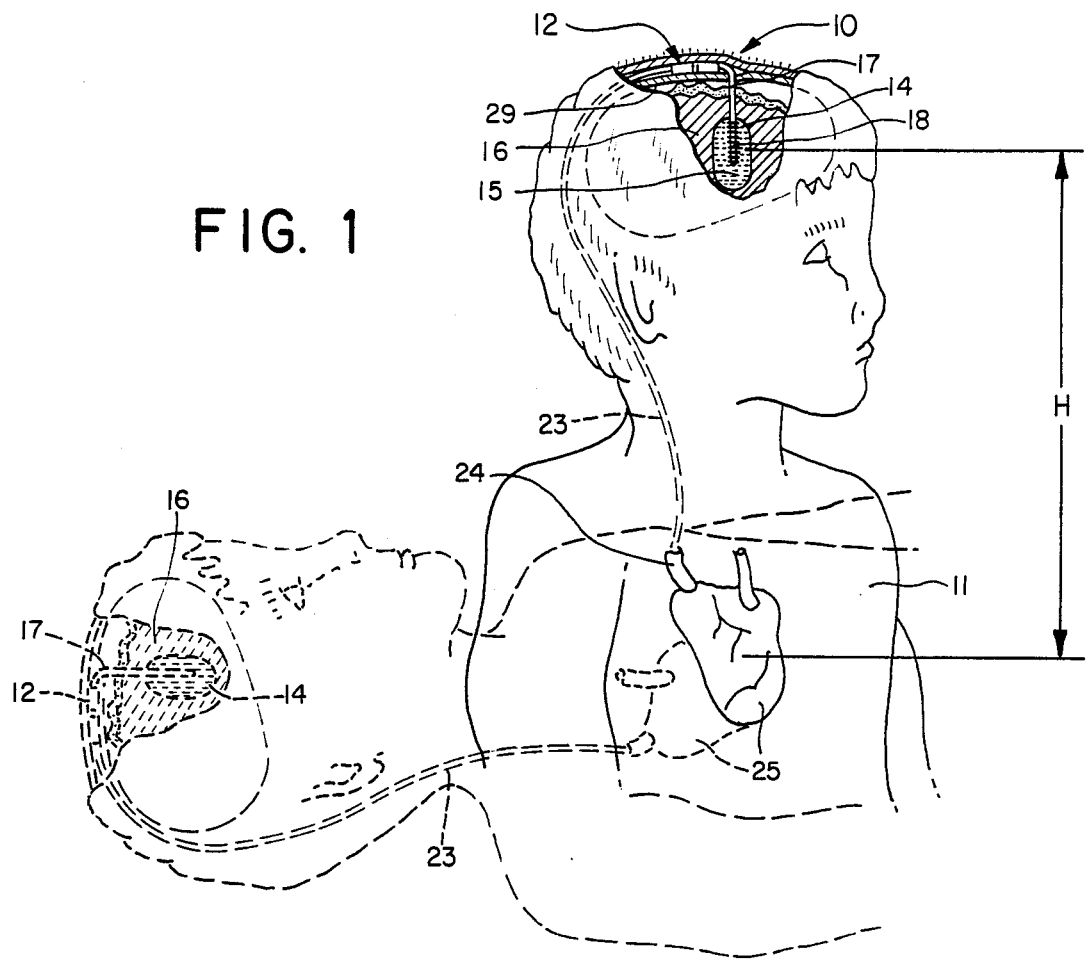
FIG. 1 is a perspective view, partially in section, of a CSF pressure relief system employing a three stage pressure regulator valve constructed in accordance with the present invention, showing such a system implanted within a patient.
Figure 2:
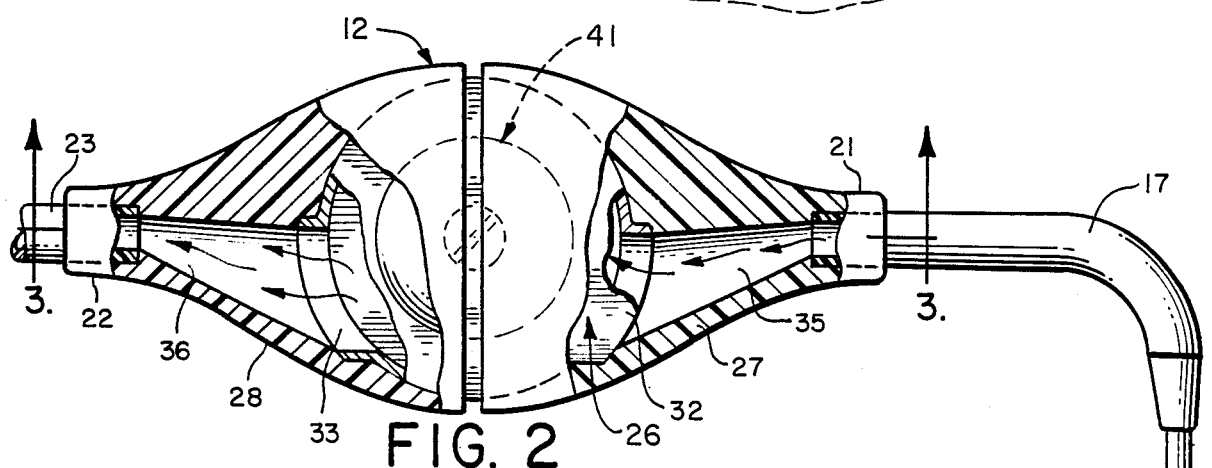
FIG. 2 is a plan view, partially in section, of the pressure regulator valve showing the principle elements thereof.
Figure 3:
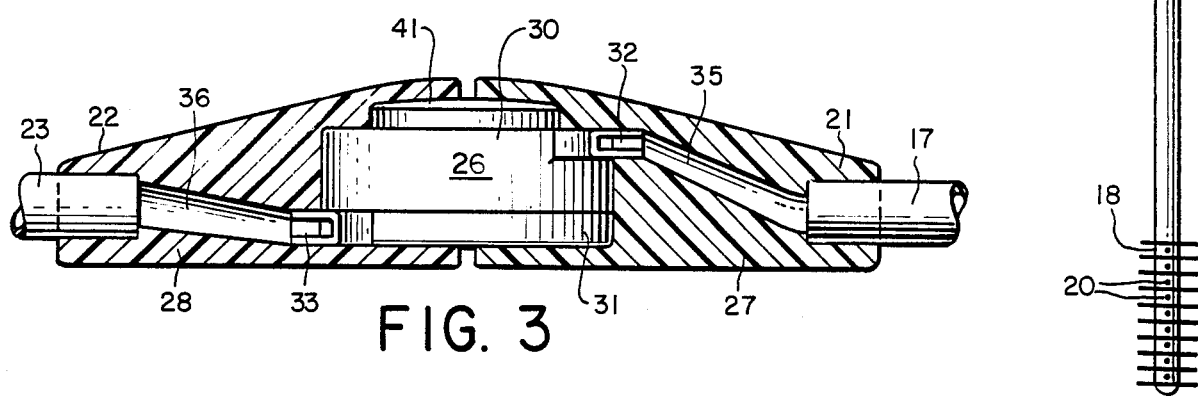
FIG. 3 is a cross-sectional view of the pressure regulator valve taken along line 3—3 of FIG. 2.

Referring to the drawings, and particularly to FIGS. 1-3, a CSF pressure relief system 10 for maintaining a desired predetermined intracranial pressure in a patient 11 is illustrated. The system shown includes a three stage pressure relief valve 12 constructed in accordance with the present invention for maintaining the desired intracranial pressure.

Cerebrospinal fluid (CSF) 14 is drained from a ventricle 15 of the brain 16 by means of a ventricular catheter 17. Preferably, the catheter is radio-opaque in order to facilitate its accurate placement with the brain. The distal end 18 of the catheter may be provided with a plurality of apertures 20 (FIG. 2) for allowing the passage of CSF therethrough and is positioned in a suitable brain ventricle as illustrated. The other end of the catheter is coupled to the inlet port 21 of the valve to establish fluid communication between the valve and the ventricle. The outlet port 22 of the valve is attached to one end of a drain catheter 23, the opposite end of which discharges into an appropriate location in the patient's body. Although the drain catheter is shown threaded through an appropriate vein 24 to terminate within the right atrium of the heart 25, a different drainage location, such as, for example, the peritoneal cavity, could be selected instead. When open, pressure relief valve 12 allows passage of CSF from the drain ventricle to the selected discharge location to relieve excessive intracranial pressure caused by excessive accumulation of CSF. Typically, pressure relief valve 12 includes means for adjusting the differential pressure threshold at which it opens so that the hydrocephalus pressure relief system can be adjusted to suit the specific requirements of an individual patient.

While an increased differential pressure may result from the excessive accumulation of CSF in the brain ventricle, such an increase might also be a perfectly normal response to ordinary physical activity of the patient. For example, when a patient stands after lying for some time in a recumbent position, as illustrated in phantom in FIG. 1, the differential pressure will suddenly increase by reason of the sudden increase in vertical height H of the fluid column existing between the distal end of the ventricular catheter and the drainage location. If the relief valve were to open and permit unrestrained fluid flow in response to this pressure increase, hyperdrainage of the ventricle, and a brain hematoma, are possible results. Accordingly, the valve increase means for preventing such unrestricted fluid flow to the drainage location in the event of a sudden increase in the differential pressure.

The internal construction and operation of the three stage valve may best be understood by reference to FIGS. 2–6. As illustrated, the valve includes a disc-shaped inner housing 26 fashioned from a durable, biologically compatible material, such as thermoplastic polymers of polyethersulfone or polycarbonates. The inner housing 26 is received within an outer housing comprising two members 27 and 28 formed of silicone rubber or a similar material bonded together over the inner housing. The dimensions of the inner and outer housings are selected so as to be compatible with subcutaneous implantation of the valve over the cranium 29 (FIG. 1).

Figure 4:
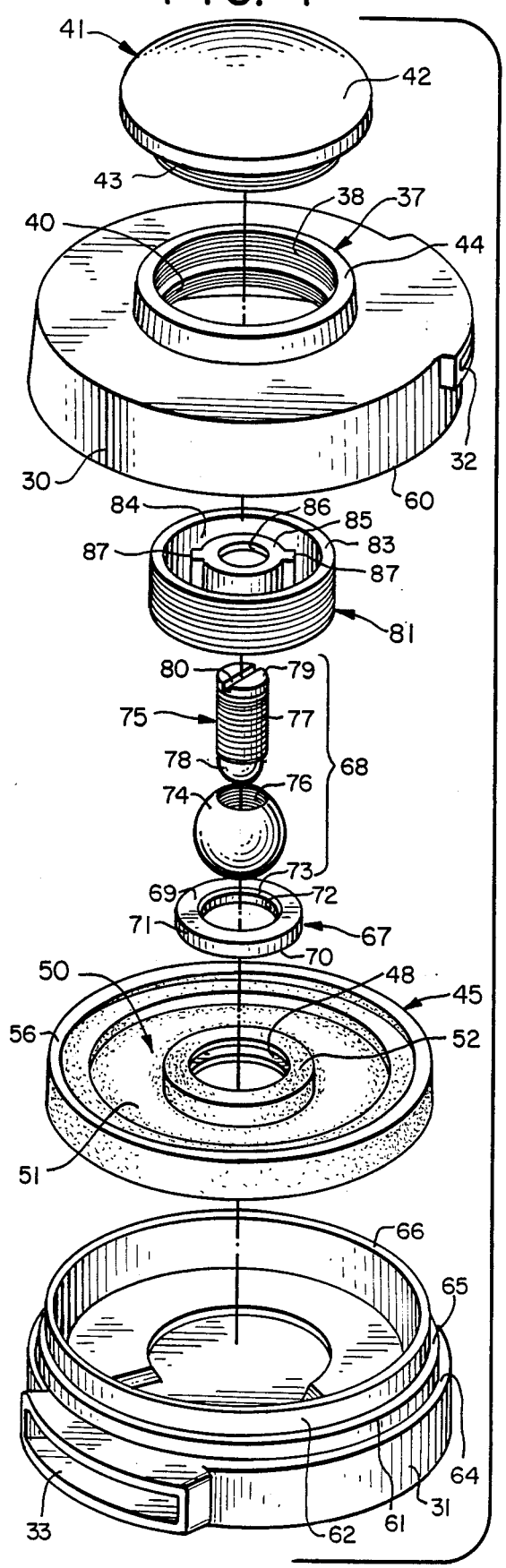
FIG. 4 is an exploded perspective view of the pressure regulator valve showing the principle elements of the present invention.
Figure 5:
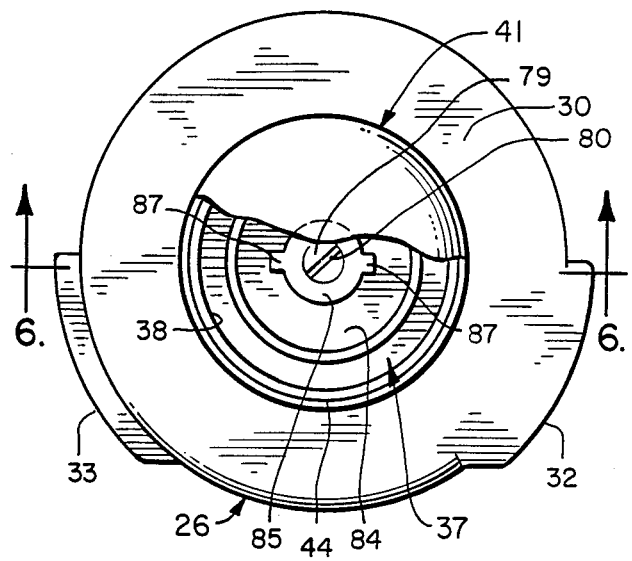
FIG. 5 is a top plan view, partially in section, of the pressure regulator valve shown in FIG. 4.

As is best illustrated in FIGS. 3 and 4, the inner housing 26 comprises two circular cup-shaped housing member 30 and 31. Housing member 30 includes an inlet port 32, and housing member 31 includes an outlet port 33, by means of which fluid can pass to or from the interior region of the housing. In this regard, outer housing members 27 and 28 are provided with internal conduits 35 and 36, which provide fluid communication between inlet port 32, outlet port 33 and housing 26, respectively.

Upper housing member 30 is provided with an aperture 37 through the upper surface thereof. As illustrated in FIG. 4, the aperture 37 includes a region 38 of relatively larger diameter coaxially aligned above a region of relatively smaller diameter 40. Both the relatively larger diameter and smaller diameter regions of the aperture are internally threaded as illustrated in order to seal the aperture while still allowing ready access to the interior region of the housing, the upper housing member 30 includes a removable cap 41 having a domed upper surface 42 and an externally threaded cylindrical lower portion 43 dimensioned to engage the threads of region 38 of aperture 37. To provide a tight seal between the cap and the housing, the upper housing member may include a raised annular seat 44 adjacent the periphery of the aperture against which the cap bears as it is turned into the upper housing member.

Referring to FIGS. 4 and 6, pressure relief valve 12 includes partition means in the form of a diaphragm 45 which extends laterally across the interior region of the inner housing to provide that region into first and second interior chambers 46 and 47 (FIG. 6), respectively. The diaphragm 45 may be fashioned from a flexible biocompatible material, such as silicone rubber, and, as best seen in FIG. 4, may comprise a disc-shaped member having an aperture 48 provided centrally therethrough. The operative surface 50 of the diaphragm is provided with an annular groove 51 concentrically aligned with the center aperture which allows the operative surface to travel vertically in response to differential pressure across the diaphragm such as might result from a difference in pressures n the first and second interior chambers.

Toward its center, and in the region immediately surrounding the aperture, the thickness of the diaphragm 45 is increased to form a raised area 52, having upper and lower surfaces 53 and 54, respectively. An annular channel 55 of rectangular cross-section is provided in the sidewall of aperture 48 between surfaces 53 and 54. The diaphragm 45 also includes an integrally formed raised circular edge 56 projecting both above and below the operative surface 50 along its outer circumference. This edge facilitates installation of the diaphragm in the housing.

In the manner in which the diaphragm is held in position relative to both the upper and lower housing members is best illustrated in FIGS. 4 and 6. The lower edge of the upper housing member is provided with a channel 57 thereby forming inner and outer sleeves 58 and 60 respectively. As illustrated, the vertical dimension of the inner sleeve 58 is less than that of the outer sleeve 60 while channel 57 is dimensioned to receive the outer raised edge portion 56 of the diaphragm. The upper edge surface of the lower housing member is provided with a pair of raised steps 61 and 62 which form concentric annular ledges 64, 65 and 66.

When assembled, the lower edge of the outer sleeve 60 contacts the first ledge 64, while the second ledge 65 is dimensioned so as to contact the outer edge portion 56 of the diaphragm when the diaphragm is in place. Similarly, the inner ledge 66 is dimensioned as to allow the diaphragm to be received in the spaced formed between the ledge and inner sleeve 58.

When assembled, upper housing member 30 interlocks with lower housing member 31 by engagement of their corresponding edges. Diaphragm 45 is received in the space provided therebetween with its periphery fixed relative to the two interior housing members. When mounted in this manner, the operative surface 50 of the diaphragm is free to travel vertically in response to a pressure differential existing between fluids contained in the first and second chambers of the stem assembly projects through the orifice at least during a portion of operation of the valve.

Still referring to FIGS. 4 and 6, the valve stem assembly 68 includes two basic elements or parts. As best viewed in FIG. 4, the first part is a ball valve portion 74 of spherical configuration, and the second part is an elongated stem or pin member 75. The ball member 74 is similar to a check valve except that, extending vertically and centrally thereof, the member is provided with an internally threaded aperture 76 designed to receive therethrough the pin member 75, the latter being provided with a central cylindrical and threaded shank portion 77 dimensioned to be threadedly received within the central aperture 76 of the ball member 74. The pin member 75 is further completed with a lower fluid flow control and restrictor portion 78 and a tap head portion 79 which is slotted at 80, the slot being adapted to receive a suitable tool to threadedly advance or retract the pin member 75 through the ball member 74.

As can best be seen in FIG. 6, the assembled condition of the pin and ball members includes the pin member 75 threadedly advanced through the central aperture 76 of the ball member 74. The lower fluid flow and restrictor portion 78 of the pin member extends below the bottom surface of the ball member 74, and the upper slotted head portion 79 of the pin member projects upwardly from the top surface of the ball member 74. The head portion 79 is accessible when the cap 41 is removed from the valve to permit the use of a suitable tool to advance or retract the pin member 75 relative to the ball member 74, thus permitting adjustment of fluid flow to the extent controlled by the lower fluid flow control portion 78 of the pin member.

The ball member 74 is suitably mounted in and affixed to a collar 81 which is externally threaded and dimensioned to engage the threads of the relatively smaller diameter segment 40 of aperture 37. The collar 81 includes a central recess 82 dimensioned to receive the ball member portion 74 of the valve stem assembly 68 in a suitably fixed manner. The collar 81 includes an outer upstanding annular rim 83 having internally thereof an annular groove 84. The collar 81 is provided with a raised centrally located ball member mounting portion 85 which includes a central aperture 86 through which the head 79 of the pin member 75 extends. The raised central portion 85 also includes oppositely positioned and outwardly projecting lugs or ears 87 which can be engaged by a suitable tool received in the groove 84 so that the collar 81 may be threadedly advanced or retracted within the upper housing member 30 relative to the diaphragm 45 and valve seat 67 to adjust closing pressure.

When no differential pressure acts on diaphragm 45, valve seat 67 contacts the bottom annular and spherical portion of the ball member 74 immediately above and surrounding the downwardly projecting stem member 75. This bottom portion of ball member 74 is at least somewhat frusto-conical in configuration and nests in and engages the top inner frusto-conical surface 73 of the valve seat 67 to completely close the orifice defined by the valve seat 67 and thereby prevent fluid flow of CSF between the first and second chambers. Because of this nesting feature of the engaging surfaces just described, considerable adjustment of closing pressure is built into the valve of the present invention. Such adjustment is obtained by advancing or retracting the collar 81 carrying the ball member 74 within the upper housing 30 relative to the diaphragm 45 and valve seat 67. As the bottom flow control and restrictor portion 78 of the valve pin member 75 is received through the valve seat 67, the inner and upper frusto-conical surface portion 73 of the valve seat 67 additionally functions as a guide for the pin member to alleviate sticking problems between the pin and seat due to the lack of concentricity of any parts of the valve. This nesting configuration thus aids in reducing cost of manufacture as well as permitting increased variation in functional characteristics of the valve.

Figure 10:
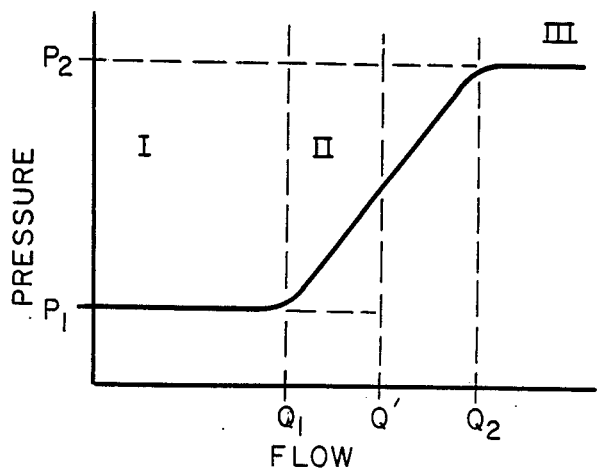
FIG. 10 is a graphical depiction of certain pressure and flow characteristics of the three stage pressure regulator valve useful in understanding the operation thereof.

FIG. 6 illustrates the operation of the valve in the absence of applied CSF pressures. FIGS. 7-9 illustrate the operation of the valve in response to various levels of CSF pressures. FIG. 10 is a graphical depiction of pressure vs. flow characteristics of the valve. Basically, the pressure regulator valve 12 normally operates to maintain a predetermined differential pressure $P_1$ between fluid in the brain ventricle and at the selected discharge location of the body. The valve accomplishes this by adjusting the fluid flow rate Q so that the pressure $P_1$ is maintained. This operation of the valve is shown in region I of FIG. 10.

When differential pressure rapidly increases, such as when the patient stands, a flow rate greater than a preselected rate $Q_1$ is necessary to maintain pressure $P_1$. However, such a flow rate may create the risk of undesirable hyperdrainage of the brain ventricle. Accordingly, when a rapid increase in differential pressure occurs, the valve automatically serves to maintain a relatively constant desired rate of fluid flow despite changes in differential pressure, as depicted in region II of FIG. 10. In a practical valve, the flow rate will not be entirely independent of the applied differential pressure but rather will increase from a lower flow rate $Q_1$ to a higher flow rate $Q_2$ as differential pressure increases between first pressure $P_1$ and a second pressure $P_2$, as indicated by the solid line in FIG. 10. Flow rates $Q_1$ and $Q_2$ are sufficiently low so that during a temporary rapid increase in differential pressure, pressure will return to normal before a quantity of CSF sufficient to cause adverse side effects may flow through the valve. In a typical valve $Q_1$ and $Q_2$ might be 0.4 ml./min., respectively, while first and second pressures $P_1$ and $P_2$, may have values of 80 and 350 millimeters of water, respectively.

While it is desirable to avoid high flow rates through the valve in order to avoid hyperdrainage of the ventricle, it may, under certain emergency conditions, be desirable to allow rapid shunting of CSF in order to avoid possible brain damage. When the valve is operating in region II, increases in differential pressure tend to close the valve between the first and second interior chambers. To avoid the possibility of building extremely high ventricular CSF pressure, the valve is constructed so that when differential pressure exceeds a predetermined pressure $P_2$ substantially higher than pressure $P_1$, the valve once again operates to allow a fluid flow rate sufficient to maintain a differential pressure on higher than the pressure $P_2$. This operation is depicted in Region III of FIG. 10. When the valve is operating in this region, further increases in differential pressure result in an increase in fluid flow through the valve thereby stabilizing differential pressure.

FIGS. 6-9 illustrate operation of the valve in the regions previously described. CSF applied to the inlet port 21 of the valve completely fills the first chamber 46 and exerts a downwardly directed force on the diaphragm 45 by reason of the CSF pressure within the brain ventricle. Since the second chamber 47 is in fluid communication with the selected drainage location in the body, the pressure of the CSF therein exerts an upwardly directed force on the lower surface of the diaphragm. Accordingly, the differential pressure between CSF in the brain ventricle and fluid at the drainage location results in vertical deflection of both the diaphragm and the valve seat 67 rigidly attached thereto.

As shown in FIG. 6, when differential pressure is negative or non-existent, valve seat 67 contacts the bottom surface portion of ball member 74 and the orifice defined by valve seat 67 is totally occluded, thereby preventing CSF flow between chambers 46 and 47. As shown in FIG. 7, differential pressure is relatively low resulting in slight downward displacement of the diaphragm sufficient to displace the valve seat 67 from the bottom portion of the ball member 74, thereby allowing CSF to pass through the orifice from chamber 46 to 47.

The bottom portion of the valve pin member 75 which defines the fluid flow control and restrictor area 78 is dimensioned so as to barely pass through the interior or orifice of the valve seat 67. By way of example, in one embodiment of the valve, the valve seat orifice had a diameter of 0.040 inches at its narrowest point and the clearance between the restrictor portion of the valve stem and the orifice at the narrowest point was on the order of 0.001 of an inch. As best illustrated in FIGS. 6-9, the bottom portion 78 of the valve pin member 75 in the direction of fluid flow is of slightly outwardly diverging frusto-conical configuration terminating in a semi-spherical end portion. While this particular configuration can vary to some degree, a suitable configuration should be used so as to obtain the fluid flow characteristics to be described. FIG. 8 illustrates the operation of the valve when a sudden increase in differential pressure is applied to the valve. When such an event occurs, the pressure differential exceeds the predetermined regulated pressure $P_1$ and the valve operates in region II of FIG. 10. The downward displacement of the diaphragm 45 is now sufficient to cause valve seat 67 to descend over the fluid flow control and restrictor portion 78 of the valve pin member 75, causing this portion to partially occlude the orifice defined by the valve seat 67. Such occlusion occurring by reason of increased differential pressure is sufficient to offset the higher flow rate ordinarily resulting from increased pressure, resulting in a relatively uniform rate of fluid flow between the chambers despite such increase in differential pressure. Accordingly, in this condition, the valve acts primarily as a constant flow device permitting the passage of fluid from chamber 46 to chamber 47 at a relatively constant predetermined rate despite changes in applied differential pressure.

FIG. 9 illustrates operation of the valve in region III of FIG. 10, such as would occur when the differential pressure exceeds a predetermined pressure level $P_2$. In this condition, differential pressure displaces the diaphragm to a degree sufficient to cause the bottom fluid flow control and restrictor portion 78 of the valve pin member 75 to extend past the upper surface of the valve seat 67 so as to allow CSF to flow past the aforesaid bottom portion and through the orifice of the valve seat. The orifice is now less restricted than in region II. When the valve is operating in this manner, increases in differential pressure cause the valve seat to be further displaced thereby further opening the orifice and allowing a greater fluid flow rate. Thus, the valve operates essentially as a constant pressure device whereby differential pressure greater than the predetermined maximum pressure $P_2$ is prevented.

The valve assembly described alleviates angle tolerance required with respect to the distance from the seating surface on the ball member 74 to the area of greatest flow restriction on the pin member 75. Adjustment of the pin member 75 relative to the ball member 74 makes this possible. As a result, closing pressure and the area of greatest flow restriction may be set independently, and the length between the seating surface and the point of greatest fluid flow restriction is no longer a design limitation. Variations in physical properties of diaphragms may also be accommodated. Assembly techniques are made much more flexible. In combination with the adjustment feature, the provision of he upwardly diverging frusto-conical inner surface 73 of the valve seat 67 provides more room within the miniaturized valve without sacrificing diaphragm travel length.

Materials to be used for this type of valve application are known. For example, the valve assembly and seat may be made of 316 stainless steel. The collar 81 may be made from appropriate polycarbonate material and the valve seat may be insert molded into the liquid silicone rubber diaphragm.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A subcutaneous implantable valve for regulating the flow of fluid from one location in the body to another location, comprising:
   a housing including an upper housing portion;
   a flexible diaphragm in said housing and dividing the same into first and second interior chambers;
   inlet port means for establishing fluid communication between said first interior chamber and the one location;
   outlet port means for establishing fluid communication between said second interior chamber and the other location;
   a valve seat forming a part of said diaphragm and providing a fluid passageway opening communicating said first interior chamber with said second interior chamber;
   said valve seat and diaphragm having a static position within said housing in the absence of a first predetermined pressure differential between said chambers;
   a combination valve closure member and valve stem fluid flow restrictor mounted in said upper housing portion and projecting into said first interior chamber in coaxial alignment with said fluid passageway, said restrictor projecting from said valve closure member and at least into close association with said valve seat for control of fluid flow through said fluid passageway opening, whereby in the static condition of said diaphragm said valve seat is in engagement with said valve closure member to establish a first valving mode wherein fluid flow through said fluid passageway is prevented in the absence of said first predetermined pressure differential between said chambers, and whereby in response to a varying pressure differential between said chambers exceeding said first predetermined pressure differential said valve seat is displaceable away from said valve closure member to move along and past said restrictor to successively establish second, third and fourth valving modes wherein fluid flow between said chambers in said second valving mode is sufficient to maintain said first predetermined pressure differential, fluid flow between said chambers in said third valving mode is at a substantially constant rate, and fluid flow between said chambers in said fourth valving mode is sufficient to prevent exceeding a second predetermined pressure differential between said chambers;
   said upper housing portion being provided with an opening through which said combination valve closure member and restrictor is advancable and retractable to permit variation in the parameter of at least said first predetermined pressure differential; and
   said valve closure member being provided with an opening through which said restrictor is advancable and retractable to permit variation in the parameter of at least said second predetermined pressure differential.

2. A flow regulating valve as defined in claim 1 wherein said valve seat is of annular configuration having a first valving surface which at least in part defines said fluid flow opening; and said restrictor is provided with successive second and third valving surfaces which coact with said first valving surface to provide said second, third and fourth valving modes.

3. A flow regulating valve as defined in claim 1 wherein said opening in said upper housing portion and said valve closure member each extend to an accessible surface area of said housing to permit access thereto from the exterior of said housing for combined or independent advancement or retraction of said valve closure member and restrictor.

4. A flow regulating valve as defined in claim 1 wherein said openings are internally threaded with said valve closure member and restrictor received therein being externally threaded for controlled advancement and retraction thereof, each of said openings further extending to an accessible surface area of said housing to permit access thereto from the exterior of said housing for combined or independent advancement or retraction of said valve closure member and restrictor; and tool engaging means formed on outer end portions of said valve closure member and restrictor to advance or retract the same.

* * * * *